US006395525B2

United States Patent
Ohto et al.

(10) Patent No.: US 6,395,525 B2
(45) Date of Patent: *May 28, 2002

(54) GERANYL DIPHOSPHATE SYNTHASE GENES

(75) Inventors: Chikara Ohto; Keishi Narita; Tokuzo Nishino, all of Sendai (JP); Shin-ichi Ohnuma, La Jolla, CA (US)

(73) Assignee: Toyota Jidosha Kabushiki Kaisha, Aichi (JP)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/367,528
(22) PCT Filed: Dec. 10, 1998
(86) PCT No.: PCT/JP98/05590
§ 371 (c)(1),
(2), (4) Date: Aug. 16, 1999
(87) PCT Pub. No.: WO99/31254
PCT Pub. Date: Jun. 24, 1999

(30) Foreign Application Priority Data

Dec. 16, 1997 (JP) .............................................. 9-346686

(51) Int. Cl.$^7$ ............................ C12N 9/10; C12N 1/20; C12N 15/00; C12P 1/00; C07H 21/04
(52) U.S. Cl. ....................... 435/193; 435/41; 435/252.3; 435/320.1; 435/832; 536/23.2
(58) Field of Search .............................. 435/193, 252.3, 435/320.1, 41, 832; 536/23.2

(56) References Cited

FOREIGN PATENT DOCUMENTS

| EP | 0733709 | * 9/1996 |
| JP | 8-214877 | 8/1996 |
| JP | 10-14567 | 1/1998 |

OTHER PUBLICATIONS

Blanchard L, Karst F: Characterization of a lysine–to–glutamic acid mutation in a conservative sequence of farnesyl diphosphate synthase from Saccharomyces cerevisiae. Gene 125: 185–189 (1993).
Chambon C, Ladeveze V, Oulmouden A, Servouse M, Karst F: Isolation and properties of yeast mutants affected in farnesyl diphosphate synthase. Curr. Genet. 18:41–46 (1990).
Chen A, Kroon PA, Foulter CD: Isoprenyl diphosphate synthases: protein sequence comparisons, a phylogenetic tree, and predictions of secondary structure. Protein Sci. 3: 600–607 (1994).
Koyama T, Obata S, Osabe M, Saito K, Takeshita A, Nishino, T, Ogura K: Thermostable farnesyl diphosphate synthase of *Bacillus stearothermophilus*: crystallization and site–directed mutagenesis. Acta Biochim. Pol. 41: 281–292 (1994).
Koyama T, Obata S, Osabe M, Takeshita A, Yokoyama K, Uchida M, Nishino T, Ogura K: Thermostable farnesyl diphosphate synthase of *Bacillus stearothermophilus*: molecular cloning, sequence determination, overproduction, and purification. J. Biochem. (Tokyo) 113:355–363 (1993).
Koyama T, Obata S, Saito K, Takeshita–Koike A, Ogura K: Structural and functional roles of the cysteine residues of *Bacillus stearothermophilus* farnesyl diphosphate synthase. Biochemistry 33:12644–12648 (1994).
Koyama T, Saito K, Ogura K, Obata S, Takeshita A: Site–directed mutagenesis of farnesyl diphosphate synthase; effect of substitution on the three carboxyl–terminal amino acids. Can. J. Chem. 72: 75–79 (1994).
Koyama T, Tajima M, Nishino T, Ogura K: Significance of Phe–220 and Gln–221 in the catalytic mechanism of farnesyl diphosphate synthase of *Bacillus stearothermophilus*. Biochem Biophys Res Commun 212: 681–686 (1995).
Koyama T, Tajima M, Sano H, Doi T, Koike–Takeshita A, Obata S, Nishino T, Ogura K: Identification of significant residues in the substrate binding site of *Bacillus stearothermophilus* farnesyl diphosphate synthase. Biochemistry 35: 9533–9538 (1996).
Marrero PF, Poulter CD, Edwards PA: Effects of site–directed mutagenesis of the highly conserved aspartate residues in domain II of farnesyl diphosphate synthase activity. J Biol Chem 267:21873–8 (1992).
Ogura K, Koyama T: Enzymatic aspects of isoprenoid chain elongation. Chemical Reviews 98:1263–1276 (1998).
Ohnuma S–i, Hemmi H, Koyama T, Ogura K, Nishino T: Recognition of allylic substrates in *Sulfolobus acidocaldarius* geranylgeranyl diphosphate synthase: analysis using mutated enzymes and artificial allylic substrates. J. Biochem. (Tokyo) 123:1036–1040 (1998).
Ohnuma S–i, Hemmi H, Ohto C, Nakane H, Nishino T: Effects of random mutagenesis in a putative substrate–binding domain of geranylgeranyl diphosphate synthase upon intermediate formation and substrate specificity. J. Biochem. 121: 696–704 (1997).

(List continued on next page.)

Primary Examiner—Tekchand Saidha
(74) Attorney, Agent, or Firm—Kenyon & Kenyon

(57) ABSTRACT

An isolated recombinant protein comprising the amino acid sequence shown in SEQ ID No: 1 is disclosed. A preferred embodiment of the invention is a recombinant protein having the amino acid sequence shown in SEQ ID NO: 1 but having a deletion, substitution or addition of at least one amino acid, excluding the amino acid at position 82, and which has geranyl diphosphate synthase activity. Also disclosed is the gene encoding the recombinant protein.

12 Claims, 4 Drawing Sheets

OTHER PUBLICATIONS

Ohnuma S–i, Hirooka K, Hemmi H, Ishida C, Ohto C, Nishino T: Conversion of product specificity of archaebacterial geranylgeranyl–diphosphate syntahse. J. Biol. Chem. 271:18831–18837 (1996).

Ohnuma S–i, Hirooka K, Ohto C, Nishino T: Conversion from archaeal geranylgeranyl diphosphate synthase to farnesyl diphosphate synthase. Two amino acids before the first aspartate–rich motifsolely determine eukaryotic farnesyl diphosphate synthase activity. J. Biol,. Chem. 272:5192–5198 (1997).

Ohnuma S–i, Hirooka K, Tsuruoka N, Yano M, Ohto C, Nakane H, Nishino T: A pathway where polyprenyl diphosphate elongates in prenyltransferase. J. Biol. Chem. 273:26705–26713 (1998).

Ohnunia S–i, Nakazawa T, Hemmi H, Hallberg AM, Koyama T, Ogura K, Nishi.no T: Conversion from farnesyl diphosphate synthase to geranylgeranyl diphosphate synthase by random chemical mutagenesis. J. Biol. Chem. 271:10087–10095 (1996).

Ohnuma S–i, Narita K, Nakazawa T, Ishida C, Takeuchi Y, Ohto C, Nishino T: A role of the amino acid residue located m the fifth position before the first aspartate–rich .motif of farnesyl diphosphate synthase on determination of the final product. J. Biol. Chem. 271:30748–30754,(1996).

Tarshis L, Proteau P, Kellogg B, Sacchettini J, Poulter C: Regulation of product chain length by isoprenyl diphosphate syntheses. Proc. Natl. Acad. Sci. U.S.A. 93:15018–15023 (1996).

M. Clastre, et al., Plant Physiology, vol. 102, No. 1, pp. 205–211 (1993).

T. Endo, et al., Phytochemistry, vol. 31, No. 7, pp. 2273–2275 (1992).

P. Matsudaira, Methods in Enzymology, vol. 182, pp. 602–613 (1991).

J.M. Wozney, Methods in Enzymology vol. 182, pp. 738–751 (1991).

Acta Biochimica Polonica, vol. 41, No. 3/1994., T. Koyama, et al.

\* cited by examiner

FIG. 4

Conserved Region I

1. 40-YSLEAGGKR
2. 38-YGALLGGKR

Conserved Region II

☆

77-MIHTY[SLIHDDLPSM]DNDDLRRGKPTN
75-CIHAY[SLIHDDLPAM]DDDLRRGLPTC

Conserved Region III

1. 159-GQAADM
2. 157-GQALDL

Conserved Region IV

183-KTGKMLQYSVHAGALIGG
181-KTGALIRAAVRLGALSAG

Conserved Region V

1. 217-GLAFQIRDDILDIEGAEEKIGKPVGSDQSNNK
2. 216-GLAFQVQDDILDVVGDTATLGKRQGADQQLGK

US 6,395,525 B2

GERANYL DIPHOSPHATE SYNTHASE GENES

TECHNICAL FIELD

The present invention relates to a geranyl diphosphate synthase, a gene encoding the synthase, a recombinant vector comprising the gene, and methods for preparing a geranyl diphosphate synthase and geranyl diphosphate, respectively.

BACKGROUND ART

Among those substances which have an important function in organisms, there are a large number of substances biosynthesized with isoprene (2-methyl-1,3-butadiene) units. These compounds are also called isoprenoids, terpenoids or terpenes. Depending on the number of carbon atoms they have, they are classified into hemiterpene (C5), monoterpene (C10), sesquiterpene (C15), diterpene (C20), sesterterpene (C25), triterpene (C30), tetraterpene (C40) and the like.

Actual biosynthesis of these substances starts with the synthesis of isopentenyl diphosphate (IPP), the active isoprene unit. Ultimately, the actual form of the isoprene unit which had been proposed as an putative precursor substance is IPP, the so-called active isoprene unit.

It is known that dimethylallyl diphosphate (DMAPP), an isomer of IPP, is synthesized into an active isoprenoid such as geranyl diphosphate (GPP), neryl diphosphate, farnesyl diphosphate (FPP), geranylgeranyl diphosphate (GGPP), geranylfarnesyl diphosphate (GFPP), hexaprenyl diphosphate (HexPP) or heptaprenyl diphosphate (HepPP), through condensation with IPP.

Through cis-condensation of FPP, GPP and the like in which the all-E type is considered to be the active type, a number of compounds such as natural rubber, dolichol, bactoprenol (undecaprenol) or various polyprenols found in plants are synthesized. It is considered that these compounds are synthesized by the consecutive condensation using the energy of phosphate bonds between the pyrophosphoric acid and the carbon skeleton in their molecules. It is considered that pyrophosphoric acid is generated as a by-product of the condensation.

Active type isoprenoid synthases which condensate IPP into allylic substrates of DMAPP, GPP, FPP, GGPP, GFPP, etc. in succession are called prenyl diphosphate synthases or prenyltransferases. Prenyl diphosphate synthases have different designations depending on the number of carbon atoms in their major reaction product. For example, the enzyme which catalyzes the production of farnesyl diphosphate with 15 carbon atoms is called farnesyl diphosphate synthase (FPP synthase); and the enzyme which catalyzes the production of geranylgeranyl diphosphate with 20 carbon atoms is called geranylgeranyl diphosphate synthase (GGPP synthase).

Various prenyl diphosphate synthase genes have already been obtained from bacteria, archaea, fungi, plants and animals. Purification, activity determination as well as gene cloning and DNA sequencing have been reported on FPP synthases, GGPP synthases, hexaprenyl diphosphate synthases, heptaprenyl diphosphate synthases, octaprenyl diphosphate synthases, nonaprenyl diphosphate synthases (solanesyl diphosphate synthases), undecaprenyl diphosphate synthases and the like.

These prenyl diphosphate synthases that are fundamental for the synthesis of important and diversified compounds from both industrial and life-scientific viewpoints are generally unstable and low in specific activity. Thus, industrial application of them could not be expected. In recent several years, however, thermostable FPP synthase genes and GGPP synthase genes have been isolated from thermophilic bacteria and archaea [A. Chen and D. Poulter (1993), J. Biol. Chem., 268 (15), 11002–11007; T. Koyama et al., (1993), J. Biochem. (Tokyo), 113 (3), 355–363; S.-i. Ohnuma et al., (1994), J. Biol. Chem., 269 (20), 14792–14797]. Thus, conditions for utilizing prenyl diphosphate synthases are now being prepared.

Enzymes which synthesize $C_{10\text{-}25}$ prenyl diphosphates are homodimers. It is relatively easy to allow them to react in vitro, and a number of reports have been made on their reaction. In those enzymes, an enzyme having activity to synthesize GPP (a $C_{10}$ prenyl diphosphate) specifically has not been isolated, though partial purification of it has been reported (L. Heide and U. Berger, 1989, Arch, Biochem. Biophys., 273 (2) 331–8). Although it has been reported that a GPP synthase was successfully purified from pig liver (J. K. Dorsey et al., 1966, J. Biol. Chem. 241 (22), 5353–5360), this enzyme catalyzes the synthesis of FPP at the same time. Thus, based on the current definition of prenyl diphosphate synthase, this enzyme should be called FPP synthase.

GPP is the first intermediate for the synthesis of many monoterpenes known and is the most important compound in the biosynthesis pathway of monoterpenes.

Both geraniol and its isomer nerol, which are representative monoterpenes, are aromatics in the major components of rose oil. Another representative monoterpene camphor which is an extract from *Cinnamomum camphora* is also used as a mothball.

However, GPP synthase gene has not been isolated yet.

Under circumstances, a technology is demanded which artificially modifies the amino acid sequence of a thermophile-derived, stable, homodimer type prenyl diphosphate synthase having a high specific activity to thereby engineer a homodimer type, thermostable prenyl diphosphate synthase which specifically catalyzes the synthesis of GPP.

As thermophile-derived prenyl diphosphate synthases, *Bacillus stearothermophilus* FPP synthase and *Sulfolobus acidocaldarius* GGPP synthase have been modified. Mutants of the *S. acidocaldarius* GGPP synthase and genes thereof were selected using as an indicator an ability to complement the glycerol metabolism ability of a HexPP synthesis-dificient *Saccharomyces serevisiae* (budding yeast) [S.-i. Ohnuma et al., (1996), J. Biol. Chem., 271 (31), 18831–18837]. Mutants of the *S. stearothermophilus* FPP synthase having GGPP synthesis activity and genes thereof were obtained using lycopene synthesis as an indicator [S.-i. Ohnuma et al., (1996), J. Biol. Chem., 271 (17), 10087–10095]. Further, 18 mutant enzymes which synthesize a number of prenyl diphosphates from GGPP to HexPP in various proportions, and genes encoding those enzymes were obtained by site-directed mutagenesis the nucleotides encoding the amino acid residue located 5 amino acid residues upstream of the Asp-rich domain conserved region I (DDXX(XX)D) [S.-i. Ohnuma et al., (1996), J. Biol. Chem., 271 (48), 30748–30754]. It has been found that the amino acid residue located 5 amino acid residues upstream of the Asp-rich domain conserved region I (DDXX(XX)D) is involved in the regulation of chain lengths of reaction products.

However, no mutant enzyme having activity to synthesize GPP specifically has been obtained yet.

DISCLOSURE OF THE INVENTION

It is an object of the invention to provide a geranyl diphosphate synthase and a gene encoding the synthase.

As a result of extensive and intensive researches toward the solution of the above problem, the present inventor has succeeded in isolating a geranyl diphosphate synthase and a gene encoding the synthase by replacing a part of the amino acid sequence of a farnesyl diphosphate synthase. Thus, the present invention has been achieved.

The present invention relates to the following recombinant protein (a) or (b):

(a) a protein consisting of the amino acid sequence shown in SEQ ID NO: 1;

(b) a protein which consists of the amino acid sequence shown in SEQ ID NO: 1 having deletion, substitution or addition of at least one amino acid excluding the amino acid at position 82, and which has geranyl diphosphate synthase activity.

Further, the present invention relates to a gene coding for the above-described recombinant protein (a) or (b).

Further, the present invention relates to a geranyl diphosphate synthase gene comprising the nucleotide sequence shown in SEQ ID NO: 2.

Further, the present invention relates to a recombinant vector comprising any of the above-described genes.

Further, the present invention relates to a transformant transformed with the above-described recombinant vector.

Further, the present invention relates to a method of preparing a geranyl diphosphate synthase comprising culturing the above-described transformant in a medium and recovering the geranyl diphosphate synthase from the resultant culture.

Further, the present invention relates to a method of preparing geranyl diphosphate comprising culturing the above-described transformant in a medium and recovering geranyl diphosphate from the resultant culture.

Further, the present invention relates to a method of preparing geranyl diphosphate comprising allowing a culture of the above-described transformant to act on isopentenyl diphosphate or an isomer thereof.

Hereinbelow, the present invention will be described in more detail.

It is known that there are five conserved regions in the amino acid sequence of a prenyl diphosphate synthase (if the synthase is a heterodimer, in the amino acid sequence of one of the sub-unit) [A. Chen et al. (1994) Protein Sci., 3 (4), 600–607]. In these five conserved regions (conserved regions I–V), there are two regions rich in aspartic acid residues to which reaction products or reaction substrates are believed to be bound. These regions are called "aspartic acid rich domains" or "Asp-rich domains". Of these, the Asp-rich domain located at the amino terminal of prenyl diphosphate synthases (i.e. located in the above-mentioned conserved region II) is designated Asp-rich domain I [sequence: DDXX(XX)D wherein the XX in parentheses may not exist], and the Asp-rich domain located at the carboxyl terminal (i.e. located in the above-mentioned conserved region V) is designated Asp-rich domain II for the purpose of discrimination.

Specific examples of prenyl diphosphate synthases containing such aspartic acid rich domains as described above include farnesyl diphosphate synthase, geranylgeranyl diphosphate synthase, hexaprenyl diphosphate synthase, heptaprenyl diphosphate synthase, octaprenyl diphosphate synthase, nonaprenyl diphosphate synthase and undecaprenyl diphosphate synthase. As more specific examples, *Bacillus stearothermophilus* farnesyl diphosphate synthase, *Escherichia coli* farnesyl diphosphate synthase, *Saccharomyces cerevisiae* farnesyl diphosphate synthase, rat farnesyl diphosphate synthase, human farnesyl diphosphate synthase, *Saccharomyces cerevisiae* hexaprenyl diphosphate synthase and the like may be enumerated. The amino acid sequences of the above-mentioned conserved regions I–V in bacterial farnesyl diphosphate synthases among those examples are shown in FIG. 4. In FIG. 4, "1." represents the amino acid sequence of *Bacillus stearothermophilus* farnesyl diphosphate synthase and "2." represents the amino acid sequence of *E. coli* farnesyl diphosphate synthase. The portion enclosed with a larger box shows Asp-rich domain I, and the portion marked with "☆" shows the amino acid residue located 4 amino acid residues upstream of this Asp-rich domain I.

The present invention is characterized by the creation of a geranyl diphosphate synthase by substituting the amino acid residue located 4 amino acid residues upstream of Asp-rich domain I with other amino acid residue having a larger molecular weight than that residue, and by the preparation of geranyl diphosphate through the enzyme reaction of the resultant geranyl diphosphate synthase. More specifically, a geranyl diphosphate synthase is created by substituting the amino acid residue marked with "☆" in FIG. 4 (Ser) located 4 amino acid residues upstream from the N-terminal amino acid (Asp) of the sequence DDXX(XX)D constituting Asp-rich domain I with other amino acid residue having a larger molecular weight than Ser (any amino acid excluding Gly and Ala; i.e. any amino acid selected from the group consisting of Val, Leu, Ile, Thr, Asp, Glu, Asn, Gln, Lys, Arg, Cys, Met, Phe, Tyr, Trp, His and Pro). The amino acid used for the above substitution is not particularly limited as long as it is neither Gly nor Ala. Preferably, Phe is used.

Specifically, the geranyl diphosphate synthase of the invention is can be obtained by substituting the Ser residue at position 82 of the amino acid sequence shown in SEQ ID NO: 5 of a farnesyl diphosphate synthase with, for example, Phe residue.

Such substitution can be achieved by partially modifying the nucleotide sequence of the gene encoding *B. stearothermophilus* FPP synthase which is reported to be highly thermostable and high in specific activity.

(1) Preparation of a Target Gene for Mutagenesis

A target gene into which a mutation is to be introduced is the gene encoding *Bacillus stearothermophilus* FPP synthase (hereinafter abbreviated to "BstFPS"). The full length nucleotide sequence of the BstFPS gene is known [T. Koyama et al., (1993) J. Biochem., 113, 355–363; SEQ ID NO: 4] and is disclosed under Accession No. D13293 in genetic information databases such as DDBJ.

Since *B. stearothermophilus* is also available from various microorganism depositories such as ATCC (ATCC 10149), the DNA of the BstFPS gene can be obtained by conventional gene cloning methods [S. Sambrook et al. (eds.), (1989) Molecular Cloning, Cold Spring Harbor Laboratory Press, New York].

Subsequently, the resultant DNA fragment is ligated to an appropriate plasmid vector (e.g. pTV118N from Takara Shuzo) to thereby prepare a plasmid DNA for mutagenesis. This plasmid DNA is designated pFPS.

(2) Synthesis of an Oligonucleotide for Mutagenesis and Introduction of a Mutation An oligonucleotide for mutagenesis is designed so that (a) the Ser codon corresponding to the amino acid residue at position 82 of BstFPS is substituted with any codon (such as Phe codon) corresponding to any amino acid other than Gly, Ala and Ser; and (b) a restriction site for BspHI (5'TCATGA 3') is newly introduced. For example, the following nucleotide sequence may be given for the oligonucleotide.

5'-CAT ACG TAC TTC TTG ATT CAT GAT GAT TTG-3' (SEQ ID NO: 6)

This nucleotide sequence is designed so that the amino acid sequence encoded by the BstFPS gene is not altered by degeneracy of codons even after the introduction of the BspHI site. Because of the introduction of this restriction site, it is possible to detect those plasmids into which a substitution mutation has been introduced by agarose gel electrophoresis of plasmid DNA after BspHI digestion.

The synthesis of the oligonucleotide may be performed with conventional chemical synthesis equipment. Preferably, the synthesized oligonucleotide is phosphorylated and then denatured (for example, by heating it at 70° C. for 10 min).

Subsequently, using the oligonucleotide as a primer, a mutation is introduced into the plasmid prepared as described above. The method of introduction of a mutation is not particularly limited. For example., a commercial kit based on the method of Kunkel [Proc. Natl. Acad. sci., USA (1985) 82, 488] (Mutan-K kit from Takara Shuzo) may be used. Alternatively, polymerase chain reaction (PCR) may be used.

A single-stranded DNA is prepared as a template, and then the oligonucleotide described above was annealed with the template as a complementary strand synthesis primer DNA to thereby obtain a double-stranded DNA. The resultant DNA is incorporated into a plasmid, with which an E. coli strain is transformed.

The gene of the invention can be easily obtained, for example, by introducing a mutation into the DNA encoding the native amino acid sequence of the synthase (SEQ ID NO: 4) by a conventional method such as site-directed mutagenesis or PCR.

For the resultant transformant clones, their nucleotide sequences are determined. This determination may be performed by any conventional method such as Maxam-Gilbert method or the dideoxy method. Usually, the determination is performed with an automated DNA sequencer based on the dideoxy method.

SEQ ID NO: 2 illustrates by way of example a nucleotide sequence for the gene of the invention. SEQ ID NOS: 1 and 3 illustrate by way of example amino acid sequences for the geranyl diphosphate synthase of the invention, which sequences may have a mutation such as deletion, substitution or addition of at least one amino acid (e.g. one or several amino acids) excluding the amino acid at position 82 (e.g. Phe) as long as the protein consisting of the mutated sequence has geranyl diphosphate synthase activity. For example, the amino acid sequence of SEQ ID NO: 1 or 3 in which the Met at position 1 is deleted is also included in the geranyl diphosphate synthase of the invention. Also, the genes encoding these geranyl diphosphate synthases are also included in the gene of the invention.

The "geranyl diphosphate synthase activity" used herein means a catalytic activity to synthesize GPP using IPP or an isomer thereof (e.g. DMAPP) as a substrate. The introduction of a mutation may be performed by the same method as described above.

Once the nucleotide sequence of the geranyl diphosphate synthase gene of the invention has been established, the gene of the invention can be obtained by chemical synthesis, or by PCR using the gene as a template, or by hybridization using a DNA fragment having a nucleotide sequence of the gene as a probe.

(3) Construction of a Vector

A recombinant vector of the invention can be obtained by ligating the gene of the invention into an appropriate vector. The vector into which the gene of the invention is to be inserted is not particularly limited as long as it is replicable in a host. A vector which may be used for the preparation of the recombinant vector of the invention can be prepared E. coli or the like by the alkali extraction method (Birnboim, H. C. & Doly, J. (1979) Nucleic Acid Res. 7: 1513) or a variation thereof. Alternatively, a commercial vector may be used as it is, or various vectors induced according to purposes may be used. For example, pBR322, pBR327, pKK233-2, pKK233-3 or pTrc99A having a pMB1-derived replication origin may be enumerated. In addition, pUC18, pUC19, pUC118, pUC119, pTV118N, pTV119N, pBluescript, pHSG298 or pHSG396 which is modified to give a greater number of copies, or a plasmid derived from pSC101, ColE1 factor, R1 plasmid or F factor may be enumerated. Further, a fusion protein expression vector such as pGEX vector or pMal vector which facilitates the purification of the expressed product may be used.

It is also possible to perform gene transfer using a virus vector (e.g. λ phage or M13 phage) or a transposon instead of a plasmid. As a phage DNA, M13mp18, M13mp19, λgt10, λgt11 or the like may be used.

The incorporation of a DNA fragment encoding the geranyl diphosphate synthase into such a vector can be performed by conventional methods using an appropriate restriction enzyme and ligase. For example, a method may be employed in which a purified DNA is digested with an appropriate restriction enzyme and then inserted into the relevant restriction site of an appropriate vector DNA for ligation.

The gene of the invention should be incorporated in the vector in such a manner that the function of the gene can be manifested. For this purpose, the vector of the invention may contain a replication origin and expression regulating sequences appropriate for the host to be used. Further, the vector may also contain a transcription promoter, transcription terminator, ribosome binding site or the like. As the promoter, Ptac, Plac or Ptrc may be used. As the terminator, rrnB terminator may be used. As the ribosome binding site, SD sequence (represented by 5'-AGGAGG-3') may be used.

As a specific example of the thus prepared plasmid vector, pFPSm described in Examples may be given.

(4) Preparation of a Transformant

A transformant of the invention can be obtained by introducing the recombinant expression vector of the invention into a host so that the gene of interest can be expressed.

The host to be used is not particularly limited as long as it can express the gene of the invention. Specific examples of the host include Escherichia or Bacillus bacteria such as E. coli, B. subtilis, B. brevis; Saccharomyces or Pichia yeasts such as S. cerevisiae, P. Pastris; filamentous fungi of the genus Aspergillus such as A. oryzae, A. niger; cultured cells of silkworm; animal cells such as COS cells or CHO cells; or plant cells.

When a bacterium such as E. coli is used as the host, preferably, the recombinant vector of the invention is capable of autonomous replication in the host and, at the same time, is composed of a transcription promoter, a ribosome binding site, the DNA of the invention and a transcription terminator. The vector may also contain a gene to control the transcription promoter.

As the promoter sequence to start the transcription from DNA to mRNA, a native sequence (such as lac, trp, bla, lpp, PL, PR, T3 or T7) may be used. In addition to these promoters, mutants thereof (e.g. lacUV5) or sequences (e.g. tac, trc, etc.) in which a native promoter sequence is artificially fused are known and may be used in the present invention.

With respect to a sequence which regulates the ability to synthesize a protein from mRNA, it is already known that the distance between the ribosome binding site (GAGG and similar sequence) to the initiation codon (ATG or GTG) is important. Further, it is well known that a terminator which commands the termination of transcription at the 3' end (e.g. rrnBT1T2) influences upon the protein synthesis efficiency in a recombinant. Therefore, in the present invention, gene expression can be performed efficiently by using these sequences.

As a method for introducing a foreign gene into a bacterium, any method of DNA introduction into bacteria may be used. For example, a method using calcium ions [Proc. Natl. Acad. Sci., USA, 69:2110–2114 (1972)], electroporation or the like may be used.

When a yeast is used as the host, YEp13, YEp24, YCp50 or the like is used as an expression vector. As a promoter used in this case, any promoter may be used as long as it can direct the expression of the gene of interest in yeasts. For example, gal1 promoter, gal10 promoter, heat shock protein promoter, MFα1 promoter or the like may be enumerated.

As a method for introducing a foreign gene into the yeast, any method of DNA introduction into yeasts may be used. For example, electroporation [Methods Enzymol., 194:182–187 (1990)], the spheroplast method [Proc. Natl. Acad. Sci., USA, 84:1929–1933 (1978)], the lithium acetate method [J. Bacteriol., 153:163–168 (1983)] or the like may be enumerated.

When an animal cell is used as the host, pcDNAI/Amp, pcDNAI or the like is used as an expression vector. In this case, the early gene promoter of human cytomegalovirus or the like may be used as a promoter.

As a method for introducing a foreign gene into the animal cell, electroporation, the calcium phosphate method, lipofection or the like may be enumerated.

As a method for introducing a foreign gene into a plant cell, the infection method using Agrobacterium is widely used. As a method for direct introduction, the protoplast method, electroporation, bombardment, etc. may be enumerated.

The recombinant vector of the invention was incorporated into *E. coli* DH5α [designation: pFPSm(S82F)/DH5α] and deposited at the National Institute of Bioscience and Human-Technology, Agency of Industrial Science and Technology (1–3, Higashi 1-Chome, Tsukuba City, Ibaraki Pref., Japan) on Dec. 12, 1997 as FERM BP-6551 under the Budapest Treaty.

(5) Production of the Geranyl Diphosphate Synthase

The geranyl diphosphate synthase of the invention can be obtained by culturing the transformant described above in a medium and recovering the synthase from the resultant culture.

The cultivation of the transformant of the invention in a medium is carried out by conventional methods used for culturing a host.

As a medium to culture the transformant obtained from a microorganism host such as *E. coli* or yeast, either a natural or synthetic medium may be used as long as it contains carbon sources, nitrogen sources and inorganic salts assimilable by the microorganism and enables effective cultivation of the transformant.

As carbon sources, carbohydrates such as glucose, fructose, sucrose, starch; organic acids such as acetic acid, propionic acid, citric acid; and alcohols such as glycerol, methanol, ethanol, propanol may be used.

As nitrogen sources, ammonia; ammonium salts of inorganic or organic acids such as ammonium chloride, ammonium sulfate, ammonium acetate, ammonium phosphate; other nitrogen-containing compounds; Peptone; meat extract; corn steep liquor, etc. may be used.

As inorganic substances, potassium dihydrogen phosphate, dipotassium hydrogen phosphate, magnesium phosphate, magnesium sulfate, magnesium chloride, sodium chloride, iron(II) sulfate, manganese sulfate, copper sulfate, calcium carbonate, calcium chloride, etc. may be used.

When *E. coli* is used as a host, the cultivation is carried out usually under aerobic conditions (such as shaking culture or aeration agitation culture) at 37° C. for 16 to 24 hrs. During the cultivation, the pH is maintained at 6 to 8. The pH adjustment is carried out using an inorganic or organic salt, an alkali solution, a buffer or the like. During the cultivation, an antibiotic such as ampicillin or tetracycline may be added to the medium if necessary.

When a microorganism transformed with an expression vector having an inducible promoter is cultured, an inducer may be added to the medium if necessary. For example, when a microorganism transformed with an expression vector having lac promoter is cultured, isopropyl-β-D-thiogalactopyranoside (IPTG) or the like may be added to the medium. When a microorganism transformed with an expression vector having trp promoter is cultured, indoleacrylic acid (IAA) or the like may be added.

As a medium to culture a transformant obtained from an animal cell as a host, commonly used RPMI1640 medium or DMEM medium, or one of these media supplemented with fetal bovine serum, etc. may be used.

Usually, the cultivation is carried out in the presence $5-10\%$ $CO_2$ at 37° C. for 2 to 20 days. During the cultivation, an antibiotic such as kanamycin or penicillin may be added to the medium if necessary.

As a medium to culture a transformant obtained from a plant cell as a host, commonly used MS medium or this medium supplemented with kanamycin, various plant hormones, etc. is used. Usually, the cultivation is carried out at 20–30° C. for 3 to 14 days.

After the cultivation, the geranyl diphosphate synthase of the invention is recovered by disrupting the microorganisms or cells if the synthase is produced in the microorganisms or cells. If the geranyl diphosphate synthase of the invention is produced outside of the microorganisms or cells, a culture supernatant is prepared by removing the microorganisms or cells by centrifugation or the like. Then, this culture (i.e. cell extract or culture supernatant) is subjected to conventional biochemical techniques used for isolating/purifying a protein. These techniques include salting out, organic solvent precipitation, gel chromatography, affinity chromatography, hydrophobic interaction chromatography and ion exchange chromatography. These techniques may be used independently or in an appropriate combination to thereby isolate and purify the geranyl diphosphate synthase of the invention from the culture.

It should be noted that the geranyl diphosphate synthase of the invention can have geranyl diphosphate synthase activity even when it is not purified from the culture. Therefore, the cell extract or culture fluid may be used as a crude enzyme solution without purification as long as it has the synthase activity.

(6) Preparation of Prenyl Diphosphate

According to the present invention, it is possible to accumulate GPP in a culture by culturing the host transformed with the DNA of the invention and to prepare GPP by recovering the accumulated GPP.

According to the present invention, it is also possible to prepare GPP by allowing the enzyme of the invention to act on IPP or DMAPP which is a substrate for the synthase. In this method, the enzyme of the invention is reacted with a reaction substrate in a solvent, particularly in an aqueous solution. Then, a prenyl diphosphate of interest is recovered from the reaction solution. As the enzyme, not only a purified enzyme but also a crude enzyme which is semi-purified to various stages or an enzyme-containing material such as cultured cells or a culture may also be used. Further, an immobilized enzyme which is obtained by immobilizing the above-mentioned enzyme, crude enzyme or enzyme-containing material by conventional methods may also be used.

As the substrate, IPP and/or DMAPP may be used. As the solvent for the reaction, water or an aqueous buffer such as Tris buffer or phosphate buffer may be used.

BRIEF DESCRIPTION OF THE DRAWINGS

FIG. 4 shows comparison of amino acid sequences of farnesyl diphosphate synthases.

BEST MODES FOR CARRYING OUT THE INVENTION

Figure 1:
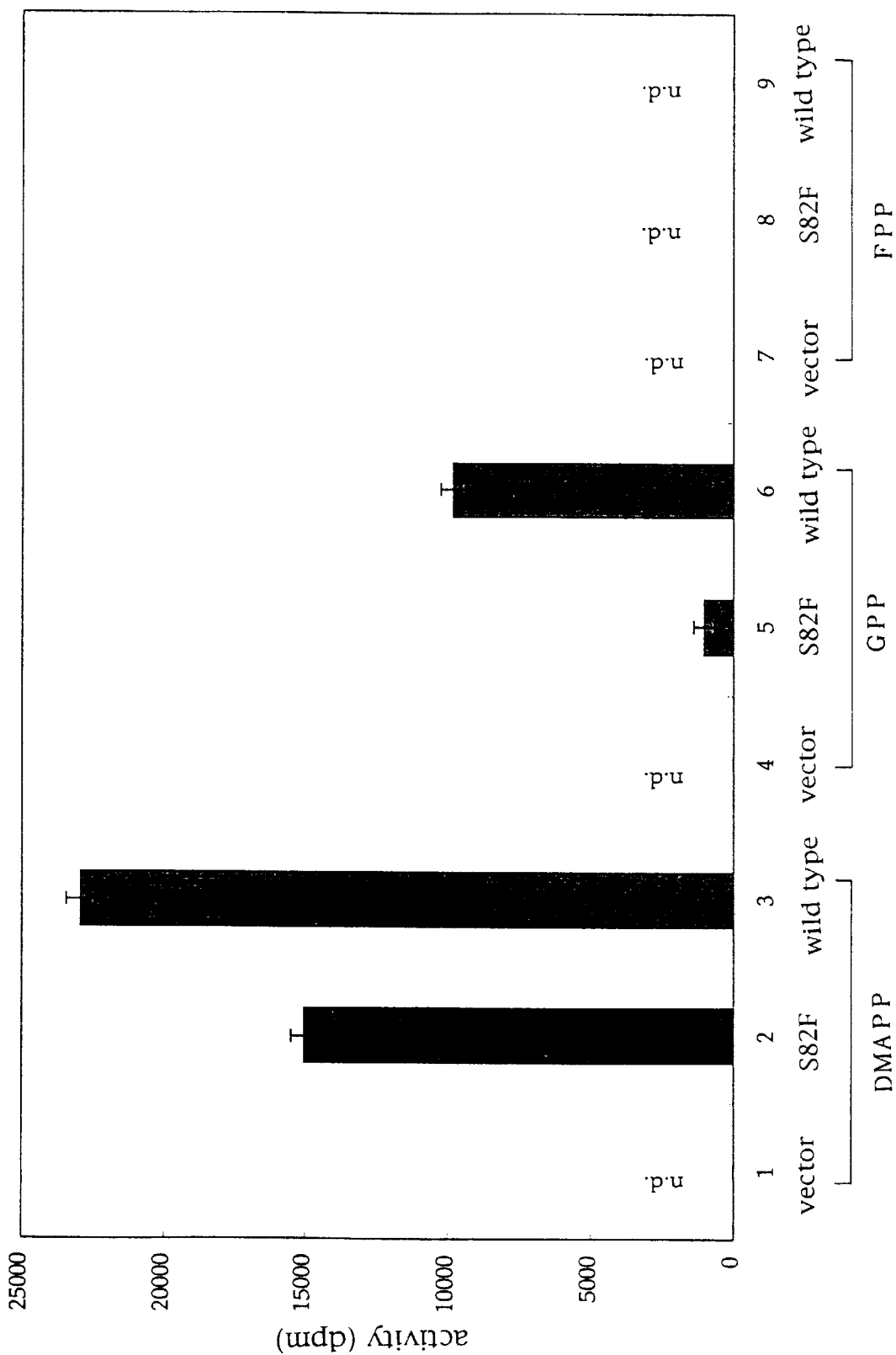
FIG. 1 is a graph showing the enzyme activity of mutant BstFPS and wild-type BstFPS.

Hereinbelow, the present invention will be described more specifically with reference to Examples. However, the technical scope of the invention is not limited to the following Examples.

Herein, amino acid residues are represented by the following one-letter or three-letter abbreviations.

A; Ala; alanine
C; Cys; cysteine
D; Asp; aspartic acid
E; Glu; glutamic acid
F; Phe; phenylalanine
G; Gly; glycine
H; His; histidine
I; Ile; isoleucine
K; Lys; lysine
L; Leu; leucine
M; Met; methionine
N; Asn; asparagine
P; Pro; proline
Q; Gln; glutamine
R; Arg; arginine
S; Ser; serine
T; Thr; threonine
V; Val; valine
W; Trp; tryptophan
Y; Tyr; tyrosine Herein, the substitution of an amino acid residue is expressed using one-letter abbreviations in the following order: "the amino acid residue before substitution", "the position of the amino acid residue" and "the amino acid residue after substitution".

For example, when Ser at position 82 is substituted with Phe, this substitution is expressed as "S82F".

EXAMPLE 1

Preparation of a Plasmid Comprising FPP Synthase Gene

*Bacillus stearothermophilus*-derived FPP synthase (BstFPS) gene was sub-cloned into the NcoI-HindIII site of a plasmid vector pTV118N (commercially available from Takara Shuzo). This plasmid DNA is designated pFPS. The full-length nucleotide sequence of BstFPS gene is disclosed by T. Koyama et al., (1993) J. Biochem., 113, 355–363 or in genetic information databases such as DDBJ under Accession No. D13293.

EXAMPLE 2

Synthesis of an Oligonucleotide for Mutagenesis

The following oligonucleotide was synthetized in order to introduce a mutation into the gene obtained in Example 1.

5'-CAT ACG TAC TTC TTG ATT CAT GAT GAT TTG-3' (SEQ ID NO: 6)

The above oligonucleotide is designed so that (a) the Ser codon corresponding to the amino acid residue at position 82 of BstFPS is substituted with Phe codon; and (b) a restriction site for BspHI (5'TCATGA 3') is newly introduced. The introduction of this BspHI site does not cause any alteration due to degeneracy of codons in the amino acid sequence encoded by BstFPS gene. Because of the introduction of this restriction site, it is possible to detect those plasmids into which a substitution mutation has been introduced by agarose gel electrophoresis of plasmid DNA after BspHI digestion.

The synthesized oligonucleotide was phosphorylated in the following reaction solution at 37° C. for 30 min and then inactivated at 70° C. for 10 min.

| | |
|---|---|
| 10 pmol/μl oligonucleotide | 2 μl |
| 10x kination buffer | 1 μl |
| 1000 mM Tris-Cl (pH 8.0) | |
| 100 mM MgCl$_2$ | |
| 70 mM DTT | |
| 10 mM ATP | 1 μl |
| H$_2$O | 5 μl |
| T4 polynucleotide kinase | 1 μl |

EXAMPLE 3

Introduction of Substitution Mutation into the Codon Corresponding to the Amino Acid Residue at Position 82 of BstFPS Gene Using the oligonucleotide synthesized in Example 2 as a primer, a substitution mutation was introduced into the plasmid prepared in Example 1 according to the method of Kunkel. In the practice of this method, Mutan-K kit commercially available from Takara Shuzo was used. Experimental procedures were according to the protocol attached to the kit.

Briefly, a single-stranded DNA in which thymine in plasmid pFPS DNA had been replaced with deoxyuracil was prepared using *E. coli* CJ-236 as a host cell.

With this single-stranded DNA as a template, the primer DNA for complementary strand synthesis (i.e. the above oligonucleotide) was annealed in the following solution.

| | |
|---|---|
| Single-stranded DNA | 0.6 pmol |
| Annealing buffer | 1 μl |
| 200 mM Tris-Cl (pH 8.0) | |
| 100 mM MgCl$_2$ | |
| 500 mM NaCl | |
| 10 mM DTT | |
| Primer DNA (from Example 2) | 1 μl |
| H$_2$O | to give a final volume of 10 μl |

Subsequently, 25 μl of extension buffer, 60 units of *E. coli* DNA ligase and 1 unit of T4 DNA polymerase were added to the solution and to synthesize a complementary strand at 25° C. for 2 hrs. The extension buffer was composed of 50 mM Tris-Cl (pH 8.0), 60 mM ammonium acetate, 5 mM MgCl$_2$, 5 mM DTT, 1 mM NAD and 0.5 mM dNTP.

Then, the reaction was terminated by adding thereto 3 μl of 0.2 M. EDTA (pH 8.0) and treating the resultant solution at 65° C. for 5 min.

EXAMPLE 4

Creation of a Transformant Whose Gene Has Substitution Mutation in the Codon Corresponding to the Amino Acid Residue at Position 82 of BstFPS Gene

*E. coli* DH5α was transformed with the DNA solution prepared in Example 3 by the calcium chloride method as described below. Briefly, the DNA solution was added to a suspension of DH5α competent cells treated with 50 mM CaCl$_2$. Then, the suspension was put on ice for 30 min.

The resultant transformants were plated on an agar plate containing ampicillin (a transformant selection marker), and cultured at 37° C. overnight. Plasmid DNA was prepared from a transformant having ampicillin resistance as a phenotype. After digestion with BspHI, the plasmid DNA was subjected to agarose gel electrophoresis to thereby select substitution mutant pFPS plasmid which has a BspHI site within the BstFPS coding region from the resultant transformants.

Subsequently, the nucleotide sequence around the codon corresponding to the amino acid residue at position 82 of BstFPS gene in the selected substitution mutant pFPS plasmid was determined by the dideoxy method. As a result, a pFPS plasmid comprising a substitution mutant BstFPS gene (SEQ ID NO: 2) in which the Ser codon at position 82 (TCT) had been replaced with Phe codon (TTC) was obtained. This mutant is designated S82F, and the plasmid pFPSm.

EXAMPLE 5

Determination of the Activity of Mutant BstFPS

Crude enzyme solutions were prepared as described below from two transformants comprising the mutant Bst-FPS gene obtained in Example 4 and wild-type BstFPS gene, respectively, and a transformant comprising vector pTV118N alone.

Cells of each transformant cultured overnight in 2x LB medium were harvested by centrifugation and suspended in a cell disruption buffer [50 mM Tris-Cl (pH 8.0), 10 mM β-mercaptoethanol, 1 mM EDTA). This suspension was sonicated and then centrifuged at 4° C. at 10,000 r.p.m. for 10 min. The resultant supernatant was thermally treated at 55° C. for 30 min to inactivate the prenyl diphosphate synthases derived from *E. coli*. The thus treated supernatant was centrifuged under the same conditions as described above to obtain a supernatant as a crude enzyme extract. This enzyme extract was reacted at 55° C. for 15 min in the following reaction solution.

| | |
|---|---|
| [1-$^{14}$C]-IPP (1Ci/mol) | 25 nmol |
| Allylic diphosphate | 25 nmol |
| (DMAPP or GPP or FPP) | |
| Tris-Cl (pH 8.5) | 50 mM |
| MgCl$_2$ | 5 mM |
| NH$_4$Cl | 50 mM |
| β-mercaptoethanol | 50 mM |
| Enzyme solution | 50 μl |
| H$_2$O | to give a total volume of 1 ml |

After the reaction, 3 ml of water-saturated butanol was added to the reaction solution to extract the reaction products into the butanol layer. To 1 ml of the resultant butanol layer, 3 ml of a liquid scintillator was added. Then, the mixture was subjected to the determination of radioactivity using a liquid scintillation counter.

The results are shown in FIG. 1. FIG. 1 is a graph showing the enzyme activity of S82F mutant BstFPS and wild-type BstFPS. Sample Nos. 1, 4 and 7 represent an enzyme prepared from a host comprising vector pTV118N alone. Sample Nos. 2, 5 and 8 represents an enzyme prepared from a host comprising a gene encoding S82F mutant BstFPS. Sample Nos. 3, 6 and 9 represent an enzyme prepared from a host comprising a gene encoding wild-type BstFPS. Further, sample Nos. 1, 2 and 3 represent the results when DMAPP was used as an allylic substrate. Sample Nos. 4, 5 and 6 represent the results when GPP was used as an allylic substrate. Sample Nos. 7, 8 and 9 represent the results when FPP was used as an allylic substrate.

From FIG. 1, it is understood that the wild-type enzyme can use DMAPP and GPP as an allylic substrate but cannot use FPP. On the other hand, it is shown that the ability to use GPP as an allylic substrate is extremely lowered in S82F mutant enzyme.

Subsequently, a reaction solution was prepared separately in the same manner as described above. Immediately after the reaction, 1 ml of a potato acid phosphatase solution [2 mg/ml potato acid phosphatase, 0.5 M sodium acetate (pH 4.7)] was added to the reaction solution, which was dephosphorylated at 37° C. and then extracted with 3 ml of pentane. The extract was analyzed by thin-layer chromatography [reversed phase TLC plate: LKC18 (Whatman); developer: acetone/water=9/1]. The developed, dephosphorylated reaction products were applied to Bioimage Analyzer BAS2000 (Fuji Photo Film) to determine the positions and relative quantities of radioactivity.

Figure 2:
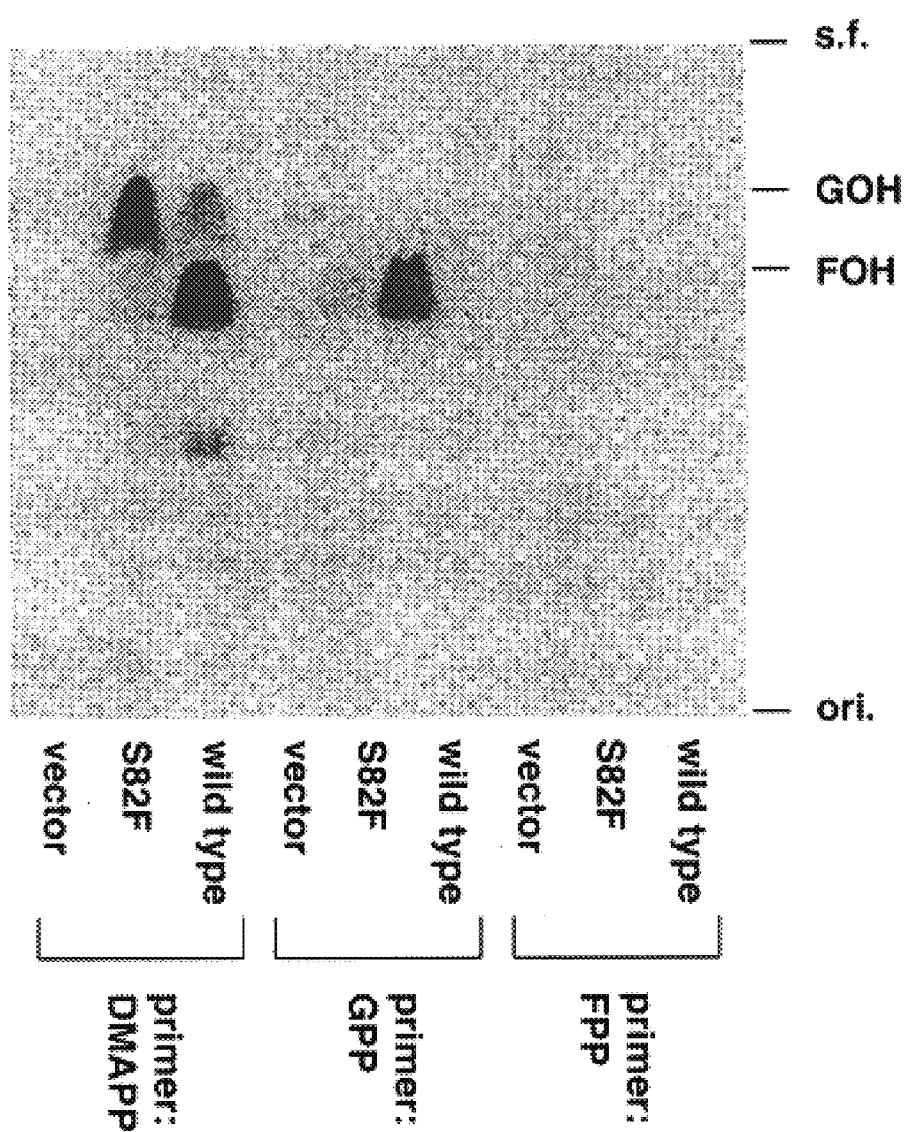
FIG. 2 is a photograph of thin-layer chromatogram.
Figure 3:
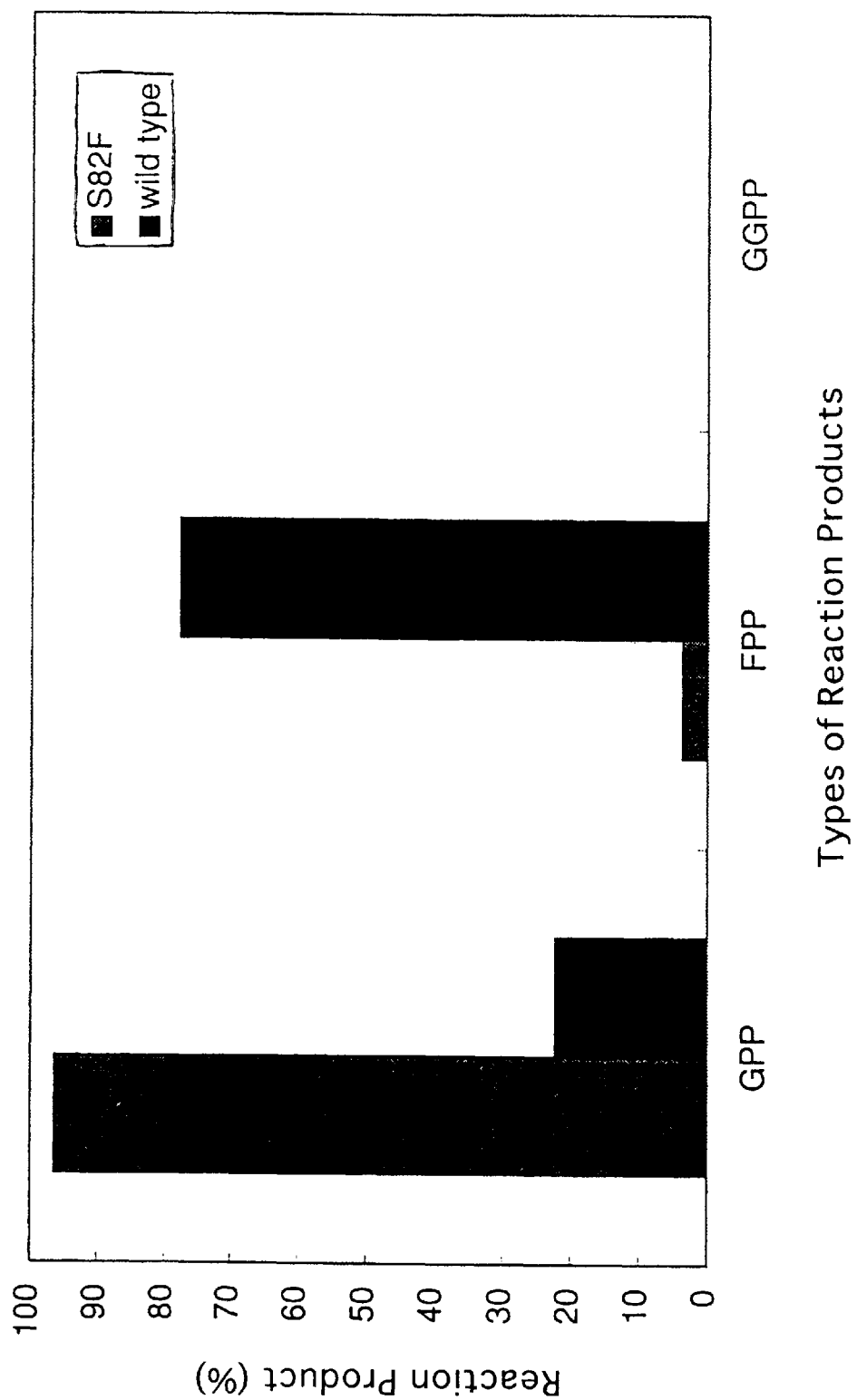
FIG. 3 is a graph showing the reaction product specificity of mutant BstFPS and wild-type BstFPS.

The results are shown in FIGS. 2 and 3. FIG. 2 shows the TLC development patterns of the dephosphorylated, mutant PstFPS reaction products when individual allylic substrates were used. For comparison, patterns obtained from samples prepared from hosts comprising wild-type BstFPS gene and a vector alone, respectively, are also shown. In this figure, "s.f." represents the solvent front; "ori" represents the development origin; "GOH" represents the position of geraniol standard sample developed; and "FOH" represents the position of farnesol standard sample developed. "Wild type" shows the results when wild-type BstFPS was used; "S82F" shows the results when mutant S82F BstFPS was used; and "vector" shows the results when an enzyme prepared from a host comprising a vector alone was used. "n.d." means that activity was not detected. FIG. 3 is a graph showing the reaction product specificity of wild-type BstFPS and mutant BstFPS. This graph shows GGPP, FPP and GPP generation ratios when IPP and DMAPP were used as a substrate.

From the results shown in FIGS. 2 and 3, it is understood that while wild-type BstFPS catalyzes a reaction to synthesize FPP specifically, S82F mutant BstFPS has been changed to catalyze a reaction to synthesize GPP specifically. This means that S82F mutant BstFPS has been changed to an enzyme that can be called a geranyl diphosphate synthase.

Industrial Applicability

According to the present invention, a geranyl diphosphate synthase, a gene encoding the synthase, a recombinant vector comprising the gene, and methods for preparing a geranyl diphosphate synthase and geranyl diphosphate, respectively, are provided.

The gene of the invention is useful since it is applicable to metabolic engineering and enzyme engineering aiming at the synthesis of monoterpenes.

Free Text to the Sequence Listing

SEQ ID NO: 1: Xaa represents Val, Leu, Ile, Thr, Asp, Glu, Asn, Gln, Lys, Arg, Cys, Met, Phe, Tyr, Trp, His or Pro.

SEQ ID NO: 6: Oligonucleotide which is designed based on the amino acid sequence of FPP synthase and has a BspHI site.

What is claimed is:

1. An isolated recombinant protein selected from the group consisting of:
   a) a protein comprising the amino acid sequence shown in SEQ ID NO: 1, and which has geranyl diphosphate synthase activity; and
   b) a protein which comprises the amino acid sequence shown in SEQ ID NO: 1 having deletion, substitution or addition of one amino acid outside of conserved regions I, II, III, IV, and V of said protein, and which has geranyl diphosphate synthase activity.

2. An isolated gene coding for the recombinant protein selected from the group consisting of:
   a) a protein comprising the amino acid sequence shown in SEQ ID NO: 1, and which has geranyl diphosphate synthase activity; and
   b) a protein which comprises the amino acid sequence shown in SEQ ID NO: 1 having deletion, substitution or addition of one amino acid outside of conserved regions I, II, III, IV, and V of said protein, and which has geranyl diphosphate synthase activity.

3. An isolated geranyl diphosphate synthase gene comprising the nucleotide sequence shown in SEQ ID NO: 2.

4. A recombinant vector comprising the gene of claim 2 or 3.

5. A transformant transformed with the recombinant vector of claim 4.

6. A method of preparing a geranyl diphosphate synthase comprising culturing the transformant of claim 5 in a medium and recovering the geranyl diphosphate synthase from the resultant culture.

7. A method of preparing geranyl diphosphate comprising culturing the transformant of claim 5 in a medium and recovering geranyl diphosphate from the resultant culture.

8. A method of preparing geranyl diphosphate comprising allowing a culture of the transformant of claim 5 to act on isopentenyl diphosphate or an isomer thereof.

9. An isolated recombinant protein comprising the amino acid sequence shown in SEQ ID NO: 1, and which has geranyl diphosphate synthase activity.

10. An isolated recombinant protein comprising the amino acid sequence shown in SEQ ID NO: 1 having deletion, substitution or addition of one amino acid outside of conserved regions I, II, III, IV, and V of said protein, and which has geranyl diphosphate synthase activity.

11. An isolated gene coding for the recombinant protein comprising the amino acid sequence shown in SEQ ID NO: 1, and which has geranyl diphosphate synthase activity.

12. An isolated gene coding for the recombinant protein comprising the amino acid sequence shown in SEQ ID NO: 1 having deletion, substitution or addition of one amino acid outside of conserved regions I, II, III, IV, and V of said protein, and which has geranyl diphosphate synthase activity.

* * * * *

SEQUENCE LISTING

```
<160> NUMBER OF SEQ ID NOS:  6

<210> SEQ ID NO 1
<211> LENGTH: 297
<212> TYPE: PRT
<213> ORGANISM: Bacillus stearothermophilus
<220> FEATURE:
<221> NAME/KEY: PEPTIDE
<222> LOCATION: 82
<223> OTHER INFORMATION: Xaa represents Val, Le u, Ile, Thr, Asp, Glu,
      Asn, Gln, Lys, Arg, Cys, Met, Phe, Tyr, Trp, His or Pro.

<400> SEQUENCE: 1

Val Ala Gln Leu Ser Val Glu Gln Phe Leu A sn Glu Gln Lys Gln Ala
  1               5                  10                  15

Val Glu Thr Ala Leu Ser Arg Tyr Ile Glu A rg Leu Glu Gly Pro Ala
                 20                  25                  30

Lys Leu Lys Lys Ala Met Ala Tyr Ser Leu G lu Ala Gly Gly Lys Arg
             35                  40                  45

Ile Arg Pro Leu Leu Leu Ser Thr Val A rg Ala Leu Gly Lys Asp
         50                  55                  60

Pro Ala Val Gly Leu Pro Val Ala Cys Ala I le Glu Met Ile His Thr
 65                  70                  75                  80

Tyr Xaa Leu Ile His Asp Asp Leu Pro Ser M et Asp Asn Asp Asp Leu
                     85                  90                  95

Arg Arg Gly Lys Pro Thr Asn His Lys Val P he Gly Glu Ala Met Ala
                100                 105                 110

Ile Leu Ala Gly Asp Gly Leu Leu Thr Tyr A la Phe Gln Leu Ile Thr
            115                 120                 125

Glu Ile Asp Asp Glu Arg Ile Pro Pro Ser V al Arg Leu Arg Leu Ile
130                 135                 140

Glu Arg Leu Ala Lys Ala Ala Gly Pro Glu G ly Met Val Ala Gly Gln
145                 150                 155                 160

Ala Ala Asp Met Glu Gly Glu Gly Lys Thr L eu Thr Leu Ser Glu Leu
                165                 170                 175

Glu Tyr Ile His Arg His Lys Thr Gly Lys M et Leu Gln Tyr Ser Val
                180                 185                 190

His Ala Gly Ala Leu Ile Gly Gly Ala Asp A la Arg Gln Thr Arg Glu
            195                 200                 205

Leu Asp Glu Phe Ala Ala His Leu Gly Leu A la Phe Gln Ile Arg Asp
        210                 215                 220

Asp Ile Leu Asp Ile Glu Gly Ala Glu Glu L ys Ile Gly Lys Pro Val
```

```
                        225                 230                 235                 240
        Gly Ser Asp Gln Ser Asn Asn Lys Ala Thr Tyr Pro Ala Leu Leu Ser
                            245                 250                 255

Leu Ala Gly Ala Lys Glu Lys Leu Ala Phe His Ile Glu Ala Ala Gln
                        260                 265                 270

Arg His Leu Arg Asn Ala Asp Val Asp Gly Ala Ala Leu Ala Tyr Ile
                    275                 280                 285

Cys Glu Leu Val Ala Ala Arg Asp His
                290                 295

<210> SEQ ID NO 2
<211> LENGTH: 894
<212> TYPE: DNA
<213> ORGANISM: Bacillus stearothermophilus
<220> FEATURE:
<221> NAME/KEY: CDS
<222> LOCATION: (1)..(894)

<400> SEQUENCE: 2 gtg gcg cag ctt tca gtt gaa cag ttt ctc aac gag caa aaa cag gcg         48
Val Ala Gln Leu Ser Val Glu Gln Phe Leu Asn Glu Gln Lys Gln Ala
  1               5                  10                  15 gtg gaa aca gcg ctc tcc cgt tat ata gag cgc tta gaa ggg ccg gcg         96
Val Glu Thr Ala Leu Ser Arg Tyr Ile Glu Arg Leu Glu Gly Pro Ala
             20                  25                  30 aag ctg aaa aag gcg atg gcg tac tca ttg gag gcc ggc ggc aaa cga        144
Lys Leu Lys Lys Ala Met Ala Tyr Ser Leu Glu Ala Gly Gly Lys Arg
         35                  40                  45 atc cgt ccg ttg ctg ctt ctg tcc acc gtt cgg gcg ctc ggc aaa gac        192
Ile Arg Pro Leu Leu Leu Leu Ser Thr Val Arg Ala Leu Gly Lys Asp
     50                  55                  60 ccg gcg gtc gga ttg ccc gtc gcc tgc gcg att gaa atg atc cat acg        240
Pro Ala Val Gly Leu Pro Val Ala Cys Ala Ile Glu Met Ile His Thr
 65                  70                  75                  80 tac ttc ttg atc cat gat gat ttg ccg agc atg gac aac gat gat ttg        288
Tyr Phe Leu Ile His Asp Asp Leu Pro Ser Met Asp Asn Asp Asp Leu
                 85                  90                  95 cgg cgc ggc aag ccg acg aac cat aaa gtg ttc ggc gag gcg atg gcc        336
Arg Arg Gly Lys Pro Thr Asn His Lys Val Phe Gly Glu Ala Met Ala
            100                 105                 110 atc ttg gcg ggg gac ggg ttg ttg acg tac gcg ttt caa ttg atc acc        384
Ile Leu Ala Gly Asp Gly Leu Leu Thr Tyr Ala Phe Gln Leu Ile Thr
        115                 120                 125 gaa atc gac gat gag cgc atc cct cct tcc gtc cgg ctt cgg ctc atc        432
Glu Ile Asp Asp Glu Arg Ile Pro Pro Ser Val Arg Leu Arg Leu Ile
    130                 135                 140 gaa cgg ctg gcg aaa gcg gcc ggt ccg gaa ggg atg gtc gcc ggt cag        480
Glu Arg Leu Ala Lys Ala Ala Gly Pro Glu Gly Met Val Ala Gly Gln
145                 150                 155                 160 gca gcc gat atg gaa gga gag ggg aaa acg ctg acg ctt tcg gag ctc        528
Ala Ala Asp Met Glu Gly Glu Gly Lys Thr Leu Thr Leu Ser Glu Leu
                165                 170                 175 gaa tac att cat cgg cat aaa acc ggg aaa atg ctg caa tac agc gtg        576
Glu Tyr Ile His Arg His Lys Thr Gly Lys Met Leu Gln Tyr Ser Val
            180                 185                 190 cac gcc ggc gcc ttg atc ggc ggc gct gat gcc cgg caa acg cgg gag        624
His Ala Gly Ala Leu Ile Gly Gly Ala Asp Ala Arg Gln Thr Arg Glu
        195                 200                 205 ctt gac gaa ttc gcc gcc cat cta ggc ctt gcc ttt caa att cgc gat        672
Leu Asp Glu Phe Ala Ala His Leu Gly Leu Ala Phe Gln Ile Arg Asp
```

```
                 210                 215                 220
gat att ctc gat att gaa ggg gca gaa gaa a aa atc ggc aag ccg gtc      720
Asp Ile Leu Asp Ile Glu Gly Ala Glu Glu L ys Ile Gly Lys Pro Val
225                 230                 235                 240 ggc agc gac caa agc aac aac aaa gcg acg t at cca gcg ttg ctg tcg      768
Gly Ser Asp Gln Ser Asn Asn Lys Ala Thr T yr Pro Ala Leu Leu Ser
                245                 250                 255 ctt gcc ggc gcg aag gaa aag ttg gcg ttc c at atc gag gcg gcg cag      816
Leu Ala Gly Ala Lys Glu Lys Leu Ala Phe H is Ile Glu Ala Ala Gln
                260                 265                 270 cgc cat tta cgg aac gcc gac gtt gac ggc g cc gcg ctc gcc tat att      864
Arg His Leu Arg Asn Ala Asp Val Asp Gly A la Ala Leu Ala Tyr Ile
            275                 280                 285 tgc gaa ctg gtc gcc gcc cgc gac cat taa                               894
Cys Glu Leu Val Ala Ala Arg Asp His
        290                 295

<210> SEQ ID NO 3
<211> LENGTH: 297
<212> TYPE: PRT
<213> ORGANISM: Bacillus stearothermophilus

<400> SEQUENCE: 3

Val Ala Gln Leu Ser Val Glu Gln Phe Leu A sn Glu Gln Lys Gln Ala
  1               5                  10                  15

Val Glu Thr Ala Leu Ser Arg Tyr Ile Glu A rg Leu Glu Gly Pro Ala
                 20                  25                  30

Lys Leu Lys Lys Ala Met Ala Tyr Ser Leu G lu Ala Gly Gly Lys Arg
             35                  40                  45

Ile Arg Pro Leu Leu Leu Leu Ser Thr Val A rg Ala Leu Gly Lys Asp
         50                  55                  60

Pro Ala Val Gly Leu Pro Val Ala Cys Ala I le Glu Met Ile His Thr
 65                  70                  75                  80

Tyr Phe Leu Ile His Asp Asp Leu Pro Ser M et Asp Asn Asp Asp Leu
                 85                  90                  95

Arg Arg Gly Lys Pro Thr Asn His Lys Val P he Gly Glu Ala Met Ala
            100                 105                 110

Ile Leu Ala Gly Asp Gly Leu Leu Thr Tyr A la Phe Gln Leu Ile Thr
        115                 120                 125

Glu Ile Asp Asp Glu Arg Ile Pro Pro Ser V al Arg Leu Arg Leu Ile
    130                 135                 140

Glu Arg Leu Ala Lys Ala Ala Gly Pro Glu G ly Met Val Ala Gly Gln
145                 150                 155                 160

Ala Ala Asp Met Glu Gly Glu Gly Lys Thr L eu Thr Leu Ser Glu Leu
                165                 170                 175

Glu Tyr Ile His Arg His Lys Thr Gly Lys M et Leu Gln Tyr Ser Val
            180                 185                 190

His Ala Gly Ala Leu Ile Gly Gly Ala Asp A la Arg Gln Thr Arg Glu
        195                 200                 205

Leu Asp Glu Phe Ala Ala His Leu Gly Leu A la Phe Gln Ile Arg Asp
    210                 215                 220

Asp Ile Leu Asp Ile Glu Gly Ala Glu Glu L ys Ile Gly Lys Pro Val
225                 230                 235                 240

Gly Ser Asp Gln Ser Asn Asn Lys Ala Thr T yr Pro Ala Leu Leu Ser
                245                 250                 255

Leu Ala Gly Ala Lys Glu Lys Leu Ala Phe H is Ile Glu Ala Ala Gln
```

```
                    260              265                270
Arg His Leu Arg Asn Ala Asp Val Asp Gly A la Ala Leu Ala Tyr Ile
        275              280              285
Cys Glu Leu Val Ala Ala Arg Asp His
        290              295

<210> SEQ ID NO 4
<211> LENGTH: 894
<212> TYPE: DNA
<213> ORGANISM: Bacillus stearothermophilus
<220> FEATURE:
<221> NAME/KEY: CDS
<222> LOCATION: (1)..(894)

<400> SEQUENCE: 4 gtg gcg cag ctt tca gtt gaa cag ttt ctc a ac gag caa aaa cag gcg      48
Val Ala Gln Leu Ser Val Glu Gln Phe Leu A sn Glu Gln Lys Gln Ala
  1               5                  10                  15 gtg gaa aca gcg ctc tcc cgt tat ata gag c gc tta gaa ggg ccg gcg      96
Val Glu Thr Ala Leu Ser Arg Tyr Ile Glu A rg Leu Glu Gly Pro Ala
             20                  25                  30 aag ctg aaa aag gcg atg gcg tac tca ttg g ag gcc ggc ggc aaa cga     144
Lys Leu Lys Lys Ala Met Ala Tyr Ser Leu G lu Ala Gly Gly Lys Arg
         35                  40                  45 atc cgt ccg ttg ctg ctt ctg tcc acc gtt c gg gcg ctc ggc aaa gac     192
Ile Arg Pro Leu Leu Leu Leu Ser Thr Val A rg Ala Leu Gly Lys Asp
     50                  55                  60 ccg gcg gtc gga ttg ccc gtc gcc tgc gcg a tt gaa atg atc cat acg     240
Pro Ala Val Gly Leu Pro Val Ala Cys Ala I le Glu Met Ile His Thr
 65                  70                  75                  80 tac tct ttg atc cat gat gat ttg ccg agc a tg gac aac gat gat ttg     288
Tyr Ser Leu Ile His Asp Asp Leu Pro Ser M et Asp Asn Asp Asp Leu
                 85                  90                  95 cgg cgc ggc aag ccg acg aac cat aaa gtg t tc ggc gag gcg atg gcc     336
Arg Arg Gly Lys Pro Thr Asn His Lys Val P he Gly Glu Ala Met Ala
            100                 105                 110 atc ttg gcg ggg gac ggg ttg ttg acg tac g cg ttt caa ttg atc acc     384
Ile Leu Ala Gly Asp Gly Leu Leu Thr Tyr A la Phe Gln Leu Ile Thr
        115                 120                 125 gaa atc gac gat gag cgc atc cct cct tcc g tc cgg ctt cgg ctc atc     432
Glu Ile Asp Asp Glu Arg Ile Pro Pro Ser V al Arg Leu Arg Leu Ile
    130                 135                 140 gaa cgg ctg gcg aaa gcg gcc ggt ccg gaa g gg atg gtc gcc ggt cag     480
Glu Arg Leu Ala Lys Ala Ala Gly Pro Glu G ly Met Val Ala Gly Gln
145                 150                 155                 160 gca gcc gat atg gaa gga gag ggg aaa acg c tg acg ctt tcg gag ctc     528
Ala Ala Asp Met Glu Gly Glu Gly Lys Thr L eu Thr Leu Ser Glu Leu
                165                 170                 175 gaa tac att cat cgg cat aaa acc ggg aaa a tg ctg caa tac agc gtg     576
Glu Tyr Ile His Arg His Lys Thr Gly Lys M et Leu Gln Tyr Ser Val
            180                 185                 190 cac gcc ggc gcc ttg atc ggc ggc gct gat g cc cgg caa acg cgg gag     624
His Ala Gly Ala Leu Ile Gly Gly Ala Asp A la Arg Gln Thr Arg Glu
        195                 200                 205 ctt gac gaa ttc gcc gcc cat cta ggc ctt g cc ttt caa att cgc gat     672
Leu Asp Glu Phe Ala Ala His Leu Gly Leu A la Phe Gln Ile Arg Asp
    210                 215                 220 gat att ctc gat att gaa ggg gca gaa gaa a aa atc ggc aag ccg gtc     720
Asp Ile Leu Asp Ile Glu Gly Ala Glu Glu L ys Ile Gly Lys Pro Val
225                 230                 235                 240
```

```
ggc agc gac caa agc aac aac aaa gcg acg t at cca gcg ttg ctg tcg         768
Gly Ser Asp Gln Ser Asn Asn Lys Ala Thr T yr Pro Ala Leu Leu Ser
            245                 250                 255 ctt gcc ggc gcg aag gaa aag ttg gcg ttc c at atc gag gcg gcg cag         816
Leu Ala Gly Ala Lys Glu Lys Leu Ala Phe H is Ile Glu Ala Ala Gln
            260                 265                 270 cgc cat tta cgg aac gcc gac gtt gac ggc g cc gcg ctc gcc tat att        864
Arg His Leu Arg Asn Ala Asp Val Asp Gly A la Ala Leu Ala Tyr Ile
            275                 280                 285 tgc gaa ctg gtc gcc gcc cgc gac cat taa                                  894
Cys Glu Leu Val Ala Ala Arg Asp His
            290                 295

<210> SEQ ID NO 5
<211> LENGTH: 297
<212> TYPE: PRT
<213> ORGANISM: Bacillus stearothermophilus

<400> SEQUENCE: 5

Val Ala Gln Leu Ser Val Glu Gln Phe Leu A sn Glu Gln Lys Gln Ala
 1               5                  10                  15

Val Glu Thr Ala Leu Ser Arg Tyr Ile Glu A rg Leu Glu Gly Pro Ala
            20                  25                  30

Lys Leu Lys Lys Ala Met Ala Tyr Ser Leu G lu Ala Gly Gly Lys Arg
        35                  40                  45

Ile Arg Pro Leu Leu Leu Leu Ser Thr Val A rg Ala Leu Gly Lys Asp
    50                  55                  60

Pro Ala Val Gly Leu Pro Val Ala Cys Ala I le Glu Met Ile His Thr
65                  70                  75                  80

Tyr Ser Leu Ile His Asp Asp Leu Pro Ser M et Asp Asn Asp Asp Leu
                85                  90                  95

Arg Arg Gly Lys Pro Thr Asn His Lys Val P he Gly Glu Ala Met Ala
            100                 105                 110

Ile Leu Ala Gly Asp Gly Leu Leu Thr Tyr A la Phe Gln Leu Ile Thr
        115                 120                 125

Glu Ile Asp Asp Glu Arg Ile Pro Pro Ser V al Arg Leu Arg Leu Ile
    130                 135                 140

Glu Arg Leu Ala Lys Ala Ala Gly Pro Glu G ly Met Val Ala Gly Gln
145                 150                 155                 160

Ala Ala Asp Met Glu Gly Glu Gly Lys Thr L eu Thr Leu Ser Glu Leu
                165                 170                 175

Glu Tyr Ile His Arg His Lys Thr Gly Lys M et Leu Gln Tyr Ser Val
            180                 185                 190

His Ala Gly Ala Leu Ile Gly Gly Ala Asp A la Arg Gln Thr Arg Glu
        195                 200                 205

Leu Asp Glu Phe Ala Ala His Leu Gly Leu A la Phe Gln Ile Arg Asp
    210                 215                 220

Asp Ile Leu Asp Ile Glu Gly Ala Glu Glu L ys Ile Gly Lys Pro Val
225                 230                 235                 240

Gly Ser Asp Gln Ser Asn Asn Lys Ala Thr T yr Pro Ala Leu Leu Ser
                245                 250                 255

Leu Ala Gly Ala Lys Glu Lys Leu Ala Phe H is Ile Glu Ala Ala Gln
            260                 265                 270

Arg His Leu Arg Asn Ala Asp Val Asp Gly A la Ala Leu Ala Tyr Ile
        275                 280                 285

Cys Glu Leu Val Ala Ala Arg Asp His
```

```
290              295
```

<210> SEQ ID NO 6
<211> LENGTH: 30
<212> TYPE: DNA
<213> ORGANISM: Artificial Sequence
<220> FEATURE:
<223> OTHER INFORMATION: Oligonucleotide designed based on the amino
      acid sequence of FPP synthetase and having the BspHI site.

<400> SEQUENCE: 6

```
catacgtact tcttgattca tgatgatttg                                30
```